US00PP13611P39

(12) United States Plant Patent
Uchneat

(10) Patent No.: US PP13,611 P3
(45) Date of Patent: Mar. 4, 2003

(54) DOUBLE IMPATIENS PLANT 'BALFIEPUNA'

(75) Inventor: Michael S. Uchneat, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/808,287

(22) Filed: Mar. 14, 2001

(65) Prior Publication Data

US 2002/0144329 P1 Oct. 3, 2002

(51) Int. Cl.[7] ..... A01H 5/00

(52) U.S. Cl. ..... Plt./317

(58) Field of Search ..... Plt./317

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct cultivar of Double Impatiens plant named 'Balfiepuna', characterized by its fully double purple flowers, upright and mounded habit, excellent basal branching and dark green leaves.

2 Drawing Sheets

LATIN NAME OF THE GENUS AND SPECIES OF THE PLANT CLAIMED

*Impatiens walleriana*

VARIETY DENOMINATION

'Balfiepuna'

BACKGROUND OF THE INVENTION

The present invention comprises a new and distinct Double Impatiens plant, botanically known as *Impatiens walleriana*, and hereinafter referred to by the cultivar name 'Balfiepuna'.

The new cultivar was developed by the inventor through a controlled breeding program in Elburn, Ill. The objective of the breeding program was the creation of impatiens cultivars which exhibit large, fully double flowers, are free-flowering and have a vigorous self-branching habit.

The female (seed) parent of 'Balfiepuna' was the proprietary *Impatiens walleriana* cultivar designated 573-1-3-1 (not patented) which exhibits a medium to vigorous habit and single, slightly cupped coral-rose flowers. The male (pollen) parent of 'Balfiepuna' was the proprietary *Impatiens walleriana* cultivar designated 3020-3-1-1 (not patented) which exhibits a vigorous loose habit, and large semi-double violet flowers.

Asexual reproduction of the new cultivar by two or three vegetative node stem cuttings has demonstrated that the characteristics of the new cultivar as herein described are firmly fixed and are retained through successive generations of such asexual propagation. Asexual propagation was carried out in West Chicago, Ill.

SUMMARY OF THE INVENTION

It was found that the cultivar of the present invention:

(a) exhibits attractive double purple flowers, (b) forms dark green foliage, (c) exhibits a good basal branching character and (d) exhibits a upright mounded growth habit.

The new cultivar of the present invention can be compared to Rosebud 'Purple Magic' (U.S. Plant Pat. No. 8,359). In side by side comparisons it is found that the new cultivar is slightly more compact, has longer peduncles, longer leaves and darker flower color as detailed in Table 1, below.

TABLE 1

| CHARACTERISTIC | 'BALFIEPUNA' | ROSEBUD 'PURPLE MAGIC' |
|---|---|---|
| LEAF LENGTH × WIDTH | 5.1 cm × 3.1 cm | 4.4 cm × 3 cm |
| PEDUNCLE LENGTH | 1.7 cm | 1.3 cm |
| FLOWER COLOR-UPPER SURFACE | Closest to N78A | 74A |

BRIEF DESCRIPTION OF THE PHOTOGRAPH

The accompanying photographs show as nearly true as it is reasonably possible to make the same in color illustrations of this type, typical flower and foliage characteristics of the new cultivar. Sheet 1 shows a close-up view of a typical flower and foliage of 'Baliepuna'. Sheet 2 shows a side perspective view of typical flowering plant of 'Balfiepuna'. The plants were grown in a greenhouse at West Chicago, Ill., U.S.A.

DETAILED DESCRIPTION

The new cultivar has not been observed under all possible environmental conditions to date. Accordingly, it is possible that the phenotype may vary somewhat with variations in the environment, such as temperature, light intensity, and day length.

The chart used in the identification of colors described herein is the R.H.S. Colour Chart of The Royal Horticultural Society, London, England. The color values were determined on Aug. 30, 2000 between 3:00 and 3:45 p.m. under natural daylight conditions. The plants were produced from cuttings taken from stock plants and grown in a double polycarbonate covered greenhouse under conditions comparable to those used in commercial practice while utilizing a soilless growth medium and maintaining temperatures of approximately 72° F. during the day and approximately 65° F. during the night. The plants used for data collection and measurements were grown for 8 weeks.

Classification:

*Botanical.*—*Impatiens walleriana* cultivar 'Balfiepuna'.

*Commercial.*—Double Impatiens.

Parentage: Proprietary seedling 573-1-3-1 (seed)× proprietary seedling 3020-3-1-1 (pollen).

Propagation:

*Type cutting.*—Two or three vegetative node stem cutting from near the center of plant

*Time to initiate roots.*—Approximately 7–14 days with the shorter times generally being experienced in the summer and the longer times in the winter.

*Time to form roots.*—Approximately 21 days.

*Root description.*—Fibrous, branching.

Plant description:

*Form.*—Upright and mounded.

*Habit of growth.*—Compact with good basal branching. A mature plant, at 8 weeks after planting of rooted cutting, commonly measures approximately 16.9 cm in height and approximately 31 cm in width.

*Branching habit.*—Basal branching.

*Foliage.*—Shape: Ovate with acute apex, attenuate base and serrate, ciliate margin. Venation pattern: Pinnate. Texture: Upper and lower surfaces are smooth. Size: Fully expanded leaves are approximately 5.1 cm in length and approximately 3.1 cm in width. Color of fully expanded leaves: Upper surface slightly darker than 137A, lower surface 138B with blotches of 184A. Petiole length is 1.4 cm.

*Stem.*—Color: 147C with overlay of 184A. Internode length is approximately 2.3 cm.

Flower description:

*Flowering habit.*—Freely flowering.

*Natural flowering season.*—Year round in greenhouse environment and spring until fall in the garden.

*Flowers borne.*—Above foliage arising from leaf axils.

*Quantity of flowers.*—Approximately 2 flowers and 2 buds per stem.

*Flower diameter.*—Approximately 3.5 cm.

*Petals.*—Shape: Obovate. Apex: emarginate. Base: Attenuate. Margin: Entire. Aspect: slightly cupped. Size: Length is 2.1 cm and width is 1.8 cm. Number: 21 per flower.

*Flower color.*—Fully opened flowers: Upper surface closest to N78A, lower surface N78A at edge and N78C in center. Very tiny area of 155D at attachment point.

*Sepals.*—Number: 4. Shape: Upper sepal is fused to underside of upper petal, lower sepal is modified to form nectary spur, lateral sepals are triangular, with smooth surfaces, entire margin, acute apex and truncate base. Color of lateral sepals: N144C.

*Spur.*—Size: Approximately 3 cm in length, 154D with overlay of 184A and tip of 59A.

*Bud.*—Shape: Ovate. Color: 72B. Length: 1.4 cm. Diameter: 1 cm.

*Peduncle.*—Length: Approximately 1.7 cm. Strength: Strong. Color: 146C.

*Reproductive organs.*—There tend to be no remaining reproductive organs. Occasional naked ovaries and occasional sterile, faciated stamen-like structures.

Seed production: Seed production has not been observed.

Disease resistance: Resistance to common diseases of Impatiens has not been observed.

I claim:

1. A new and distinct cultivar of *Impatiens walleriana* plant named 'Balfiepuna' substantially as herein shown and described, which:

(a) exhibits attractive, double purple flowers, (b) forms dark green foliage, (c) exhibits a good basal branching character, and, (d) exhibits a upright mounded growth habit.

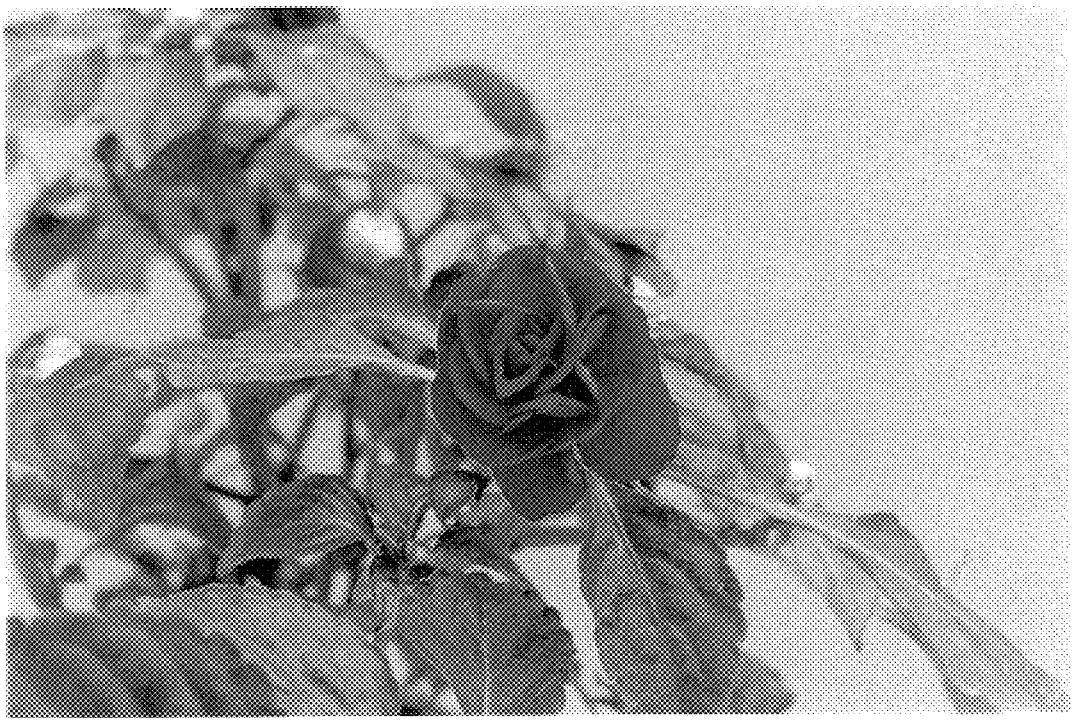

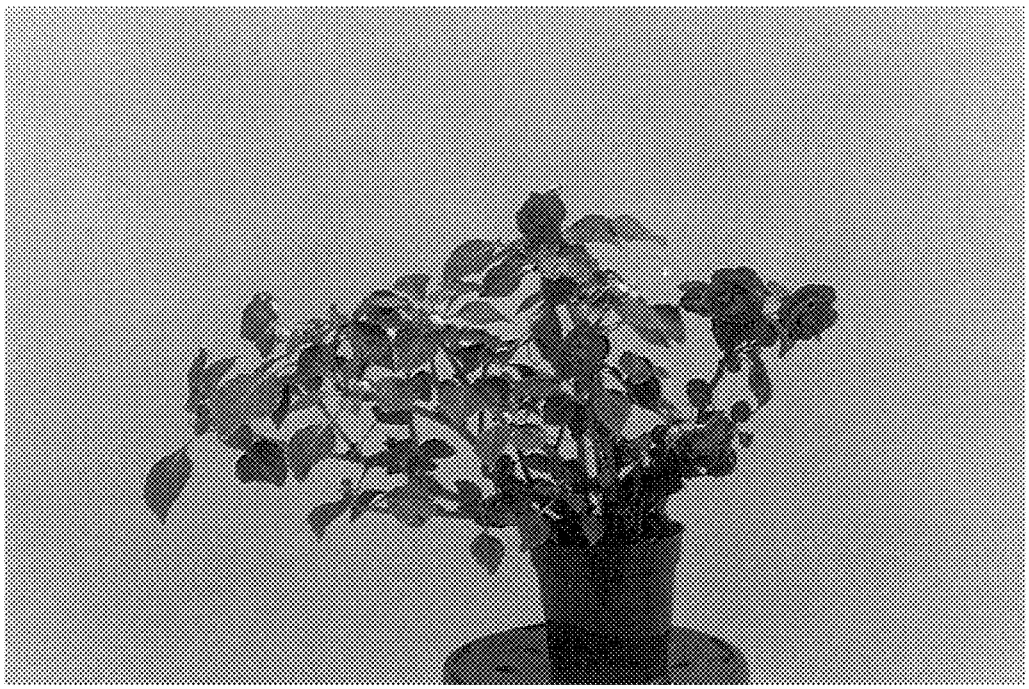

* * * * *